US005360741A

United States Patent [19]

Hunnell

[11] Patent Number: 5,360,741

[45] Date of Patent: Nov. 1, 1994

[54] DNA HYBRIDIZATION INCUBATOR

[75] Inventor: Jack E. Hunnell, Durham, N.C.

[73] Assignee: Triangle Biomedical Sciences, Inc., Durham, N.C.

[21] Appl. No.: 953,727

[22] Filed: Sep. 29, 1992

[51] Int. Cl.[5] ........................ C12M 1/38; C12Q 1/68; B01L 3/00

[52] U.S. Cl. ........................................ 435/290; 435/6; 435/809; 422/99; 422/136; 422/156; 935/85; 935/86; 935/87; 935/88

[58] Field of Search .......................... 435/6, 290, 809; 422/136, 156, 99; 935/85–88

[56] References Cited

U.S. PATENT DOCUMENTS

| | | | |
|---|---|---|---|
| 5,061,448 | 10/1991 | Mahe et al. | 422/99 |
| 5,187,084 | 2/1993 | Hallsby | 435/91 |

OTHER PUBLICATIONS

Bellco Autoblot TM specification; product sheet.
Product sheet entitled: "Bellco AutoBlot Hybridization Oven", 2 pages, Bellco Glass, Inc. (Vineland, N.J.).
Product sheets (4 pages) for The GFL ® Hybridization Incubator 7601 (distributed by Man–Tech Associates, Inc. (Buffalo, N.Y.).
Product brochure (4 pages) entitled Robbins Scientific ® Model 310 Hybridization Incubator. Robbins Scientific Corp. Sunnyvale, Calif.
Techne HB–1 Hybridization Incubator (Daigger Scientific ® Products, Manassas, Va. Bulletin 1003.
Hybridizer TM 600 Hybridization Oven (Stratagene Corporation.
Hybaid Mini Hybridization System (National Labnet Co., Woodbridge, N.J. (4 pages).

*Primary Examiner*—Margaret Parr
*Assistant Examiner*—Bradley L. Sisson
*Attorney, Agent, or Firm*—Steven J. Hultquist

[57] ABSTRACT

A hybridization incubator, of a type usefully employed to perform blot nucleic acid and protein/antibody hybridizations and stringency washes for blot procedures such as Northern, Southern, Dot, Slot, Colony, and Western blot techniques, wherein the hybridization incubator comprises an incubator chamber of irregular geometric shape. In a specific embodiment, the hybridization incubator comprises: (a) a housing including walls and a door cooperatively defining an enclosed interior volume within the housing, wherein the interior volume is bounded by segmented wall surfaces forming at least one obtuse included angle between adjacent wall segments; (b) a rotational carousel assembly constructed and arranged for holding hybridization sample(s) thereon, and mounted in the interior volume within the housing; (c) means for selectively rotating said rotational carousel assembly; and (d) means for heating gas and circulating heated gas in the interior volume of the housing over the segmented wall surfaces.

14 Claims, 3 Drawing Sheets

DNA HYBRIDIZATION INCUBATOR

BACKGROUND OF THE INVENTION

1. Field of the Invention

The invention relates to a DNA hybridization incubator, of a type usefully employed to perform blot DNA hybridizations and stringency washes for Southern, Northern, and Western blot procedures.

2. Description of the Related

The study of gene structure, function, and expression involves the extensive use of DNA and RNA hybridization techniques, in which these nucleic acids are hybridized to suitable radioactive nucleic acid probes.

In such techniques, nucleic acids to be studied may be separated according to size by electrophoresis in a gel medium, e.g., agarose gel, and the resulting separated nucleic acid is immobilized by transfer to a suitable immobilization medium such as nitrocellulose paper or a polymeric membrane. The separated blots then may be washed in a buffer medium containing the radioactive probe, e.g., a $^{32}$P-labeled DNA probe, which selectively hybridizes to the nucleic acid molecules complementary in nucleotide sequence to the probe.

The hybridization of DNA and RNA probes with nucleic acid on filter media involves Southern and Northern blotting techniques. In a related technique applicable to the study of proteins, termed Western blotting, protein blots are incubated with antibodies.

In these various hybridization procedures, depending on reagent (buffer) compositions employed, and the similarity of the probe and target molecules, the temperatures employed may variously range from about ambient temperature to about 70° C. Temperature is usefully employed as a process variable in altering the hybridization stringency. At the lower end of the aforementioned temperature range, heterologous probes are effectively used, while at the high end, target sequences which are substantially identical to the nucleotide sequence of the probe are required for the hybridization.

Typically, nucleic acid and protein hybridizations are carried out in a closed container in a constant temperature environment for extended periods of time, e.g., 10–18 hours.

The prior art has utilized various heating systems and arrangements for hybridization, including: (i) plastic bags with water baths, in which the plastic bags containing the blots and buffer medium are introduced to a constant temperature shaking water bath, with the shaking serving to produce temperature uniformity and to effect intimate contacting of the blots with the buffer medium; (ii) conventional ovens, with agitation of the buffer/blot medium contained therein; and (iii) so-called hybridization incubators, in which a rotisserie or rack is mounted in a temperature-controlled convection heating enclosure, and is driven in continual movement during the heating operation.

In relative merit, hybridization incubators have major advantages over plastic bag/water bath systems and conventional ovens with ancillary stirring or agitation of the blot/buffer medium, and have come into increasingly widespread usage in recent years. Various commercialized hybridization incubators are described below.

The BELLCO® AutoBlot™ Hybridization Oven, commercially available from BELLCO Glass, Inc. (Vineland, N.J.) is a hybridization apparatus designed for incubation/washing experiments requiring the use of membranes, including Northern, Southern, Dot, Slot, Colony, and Western blot techniques. This oven features a rotisserie oriented with its axis of rotation parallel to the front door of the oven. The rotisserie accommodates a multiplicity of incubator bottles thereon, and is removable from the oven cavity. A slip clutch is provided in the rotisserie drive mechanism to permit removal of the rotisserie from the oven even when the rotisserie drive mechanism is actuated. Forced air circulation is employed to ensure temperature uniformity, and minimize the occurrence of "hot spots" in the oven chamber.

The GFL® Hybridisation Incubator 7601 (distributed by Man-Tech Associates, Inc. (Buffalo, N.Y.)) is an incubator device utilizing forced air circulation means and a rotating rack including two large round discs with holes around their edges to enable insertion of hybridization tubes into the rack. Two wheels with spring clips mounted between these two discs hold the hybridization tubes. The clip wheel on one side can be slid along the axle, and additional clip wheels can be added to accommodate shorter hybridization tubes and to increase the incubator unit's capacity.

The Robbins Scientific® Model 310 Hybridization Incubator features a digital proportional-integral-derivative controller which measures and controls the incubator chamber temperature. A separate temperature sensor output is provided for continuously recording chamber temperature of the unit by an optional recorder. A tridirectional rotator comprising a ferris wheel clamp assembly is disposed in the chamber, on which multiple glass tubes are mounted for rotation, with the tubes being resultingly rotated about the main central axis of the rotator, as well as rotation about the glass tube axis, and with the tubes also being imparted with a back-and-forth movement, so that in Western blot procedures the blot proteins are exposed to a continuously moving thin film of antisera.

Other hybridization incubator apparatuses which are commercially available include: the Techne HB-1 Hybridization Incubator (Daigger Scientific Products, Manassas, Va.); the Hybridizer™ 600 Hybridization Oven (Stratagene Corporation, San Francisco, Calif.); and the Hybaid Mini Hybridization System (National Labnet Company, Woodbridge, N.J.).

In all of the above-described incubator structures, the heating (oven) chamber is essentially a conventionally configured gravity- or forced-convection oven with a rotisserie or rotator structure mounted or placed in a chamber of square or rectangular cross-section along each of its three major (x,y,z) axes.

These hybridization incubators, although a major advance over the aforementioned plastic bag and water bath systems, and an improvement over use of agitated containers in ovens per se, nonetheless are characterized by the inability to consistently and reliably achieve and maintain a selected temperature uniformity (throughout the entire volume of the incubator chamber), stability (over the duration of the hybridization or wash procedure), and accuracy (relative to the selected chamber temperature) within a tolerance of about ±0.5° C. or less.

This is a particular shortcoming in many applications in which the temperature must be varied according to a rigorous time-temperature schedule in order to satisfactorily carry out the procedure, with only a low tolerance in the temperature variations and deviations being permitted.

Accordingly, it is an object of the present invention to provide an improved hybridization incubator which is optimally configured to achieve better temperature uniformity, stability, and accuracy than has heretofore been possible with the hybridization incubator apparatuses of the prior art.

It is another object of the present invention to provide a hybridization incubator which is of an improved configuration with respect to its safety and maintenance characteristics, over hybridization incubators of the prior art.

Other objects and advantages of the invention will be more fully apparent from the ensuing disclosure and appended claims.

SUMMARY OF THE INVENTION

In a broad aspect, the invention relates to a hybridization incubator, of a type usefully employed to perform blot nucleic acid and protein/antibody hybridizations and stringency washes for blot procedures, e.g., Northern, Southern, Dot, Slot, Colony, and Western blot techniques, wherein the hybridization incubator comprises an incubator chamber or temperature-controlled zone of irregular geometric shape.

As used in such context, the term "irregular geometric shape" refers to a chamber or zone including at least two walls or wall segments bounding the interior volume of the chamber or zone which are neither parallel nor perpendicular to one another. Preferably, the chamber or zone includes at least two walls or wall segments defining an obtuse included angle between adjacent wall surfaces of the walls or wall segments, i.e., an included angle which is greater than 90° and less than 180°. More preferably, the chamber of the incubator includes a polygonal, generally domed upper portion defining an interior volume bounded by segmented wall surfaces forming at least one obtuse included angle between adjacent wall segments.

In one aspect, the invention relates to a hybridization incubator, suitable for nucleic acid hybridization and/or protein/antibody hybridization, comprising:

(a) a housing including walls and a door cooperatively defining an enclosed interior volume within the housing, wherein the interior volume is bounded by segmented wall surfaces forming at least one obtuse included angle between adjacent wall segments;

(b) a rotational carousel assembly constructed and arranged for holding hybridization sample(s) thereon, and mounted in the interior volume within the housing;

(c) means for selectively rotating the rotational carousel assembly;

(d) means for heating gas and circulating heated gas in the interior volume of the housing over the segmented wall surfaces.

In a particularly preferred aspect of the incubator described above, the gas heating and circulating means (d) may suitably comprise a gas discharge structure producing bifurcated gas flow in the interior volume of the housing comprising opposingly directed gas flow streams over the segmented wall surfaces.

The incubator may for example be constructed so that the housing includes walls defining a polygonal housing chamber in elevational view, and a front door hingedly joined and fastenably securable to the walls.

By way of example, the walls of the chamber may each be planar, and include:

a horizontal floor wall;

two vertical side walls, each extending from a first end joined to a differing extremity of the floor wall, and extending upwardly to a second end, each of the side walls being of a same height;

two side angle walls, each joined at a first end thereof to a second end of a different vertical side wall, and extending angularly upwardly to a second end, with the second ends of the side angle walls being in transversely spaced-apart relationship to one another; and a horizontal top wall having first and second ends, with the first end of the horizontal top wall being joined to the second end of one of said side angle walls, and with the second end of the horizontal top wall being joined to the second end of the other of said side angle walls.

In such incubator, the included angle formed between each of the vertical side walls and the side angle wall joined thereto, may be 120°, and the included angle formed between each of the side angle walls and the horizontal top wall may also be 120°.

In another aspect of the incubator broadly described above, the rotational carousel assembly may be secured by a mounting structure to one of the segmented wall surfaces.

In another aspect of the invention relating to the incubator broadly described above, the rotational carousel assembly may comprise a cylindrical carousel including a central cylindrical spindle with first and second ends, and a generally circular end plate coaxially joined to the central cylindrical spindle at each of the first and second ends, each generally circular end plate having a multiplicity of openings therein for receiving sample containers, wherein the openings in each of the end plates are in axial registration with corresponding openings in the other one of the end plates, and wherein the openings are of circular shape, to accommodate the axial positioning of cylindrical sample containers therein such that end portions of a sample container repose in registered circular-shape openings of the respective end plates.

In a preferred aspect of the incubator broadly described hereinabove, the means for rotating the rotational carousel assembly are constructed and arranged to rotate the rotational carousel assembly in a direction of rotation opposing a direction of gas flow of a gas flow stream in the interior volume within the housing.

Other aspects and features of the invention will be more fully apparent from the ensuing disclosure and appended claims.

DETAILED DESCRIPTION OF THE INVENTION, AND PREFERRED EMBODIMENTS THEREOF

Figure 1:
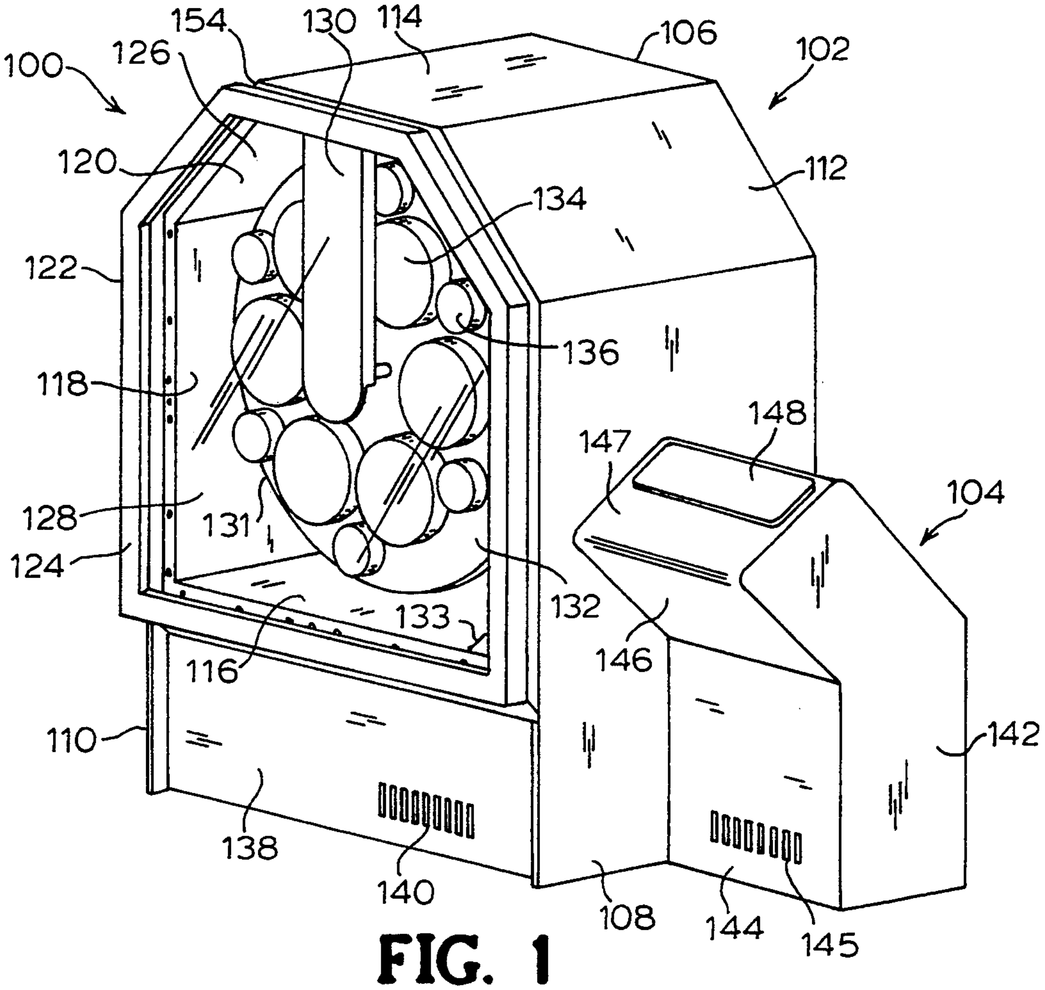
FIG. 1 is a perspective view of a hybridization incubator according to one embodiment of the present invention.

Referring now to the drawings, showing various illustrative embodiments of the present invention, FIG. 1 is a perspective view of a hybridization incubator 100 according to one embodiment of the invention.

The hybridization incubator 100 comprises a main incubator module 102 and an electronics/control module 104 which is operatively coupled to the main incubator module 102 for operation of the unit in an automatic and controllable manner.

The main incubator module 102 as shown comprises a housing 106 defining therewithin an incubator chamber 128. The housing suitably may be of doubled-walled construction, having an insulative medium between the respective inner and outer walls, e.g., a multilayer foil/paper superinsulation material, or a low conductivity (insulative) medium such as perlite, fiberglass batting, or the like.

The outer wall of the incubator housing comprises the vertical, upwardly extending side walls 108 and 110, which may be joined at their lower edges to a suitable bottom wall (not shown), or alternatively the housing 106 may be open on its bottom portion, and having a recessed bottom wall in close proximity to the chamber 128, by way of accommodating the air blower, heating means, and the like which are disposed beneath the chamber 128 within the housing below the chamber floor 116 and any associated floor or wall beneath such chamber floor member.

The lower portion of housing 106 includes front panel 138 having a grill 140 therein to accommodate exhaust from the air blower, as hereinafter more fully described.

Joined to the upper ends of side walls 108 and 110 are convergent wall segments 112 and 154. Walls 112 and 154 extend convergently toward the upper extremity of housing 106, and are joined at their upper and inner edges with top wall 114, whereby the housing has the polygonal configuration shown.

As indicated, the housing 106 may be of doubled-walled character, and in the embodiment shown the incubator chamber 128 is bounded by interior wall members or wall segments, including floor 116, side wall 118, and upper wall segment 120.

As shown in the front elevation view of FIG. 2, wherein the carousel shown in FIG. 1 has been omitted for clarity of description, the bounding walls of the chamber 128 include top horizontal wall 152, angular upper wall 121, and vertical side wall 150, in addition to angular upper wall 120, vertical side wall 118 and floor 116 shown and described with reference to FIG. 1.

Figure 2:
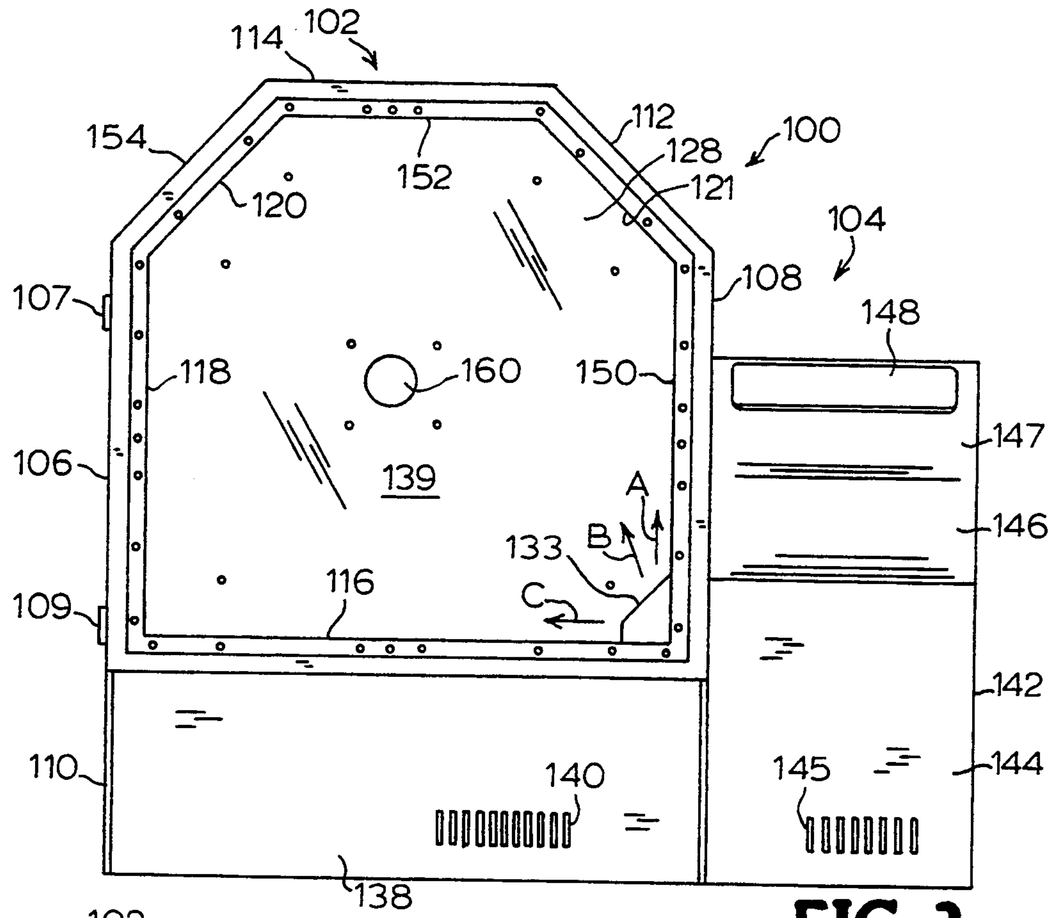
FIG. 2 is a front elevation view of the hybridization incubator of FIG. 1, wherein the carousel has been removed for clarity of description.

At the rear wall 139 of the chamber 128, as shown in FIG. 2, a cutout opening 160 is provided for accommodating the drive means employed for driving the carousel 131 (see FIG. 1).

The carousel 131 as shown in FIG. 1 comprises a front circular disk member 132 and has a series of openings therein to accommodate insertion thereinto of hybridization containers 134 and 136, whereby varying hybridization medium volumes can be accommodated in the carousel. The carousel 131 is mounted on vertical support 130 at its lower end, in a manner allowing free rotation of the carousel in a desired direction of rotation (e.g., clockwise or counterclockwise).

The support 130 at its lower portion includes suitable bearing means whereby the main central shaft (not shown) of the carousel is journaled or otherwise disposed in such bearing to accommodate a low friction rotational movement of the carousel in operation.

At the lower right-hand portion of the chamber 128 as best shown in FIG. 2, is provided a heated gas discharge unit 133 which is operatively coupled to suitable gas heating and supply means (not shown). Unit 133 is suitably louvered, vented, or otherwise provided with gas discharge ports for discharging gas in a selected flow path configuration, as for example in the directions indicated by arrows A, B, and C in the drawing.

In a particularly advantageous embodiment of the invention, the discharge unit 133 is suitably configured to discharge gas in multiple directions, as for example predominantly in the directions indicated by arrows A and C, whereby heated gas flow around the periphery of the carousel is produced, to thereby minimize temperature gradients, and to ensure a temperature uniformity and stability to a tolerance of within about ±0.5° C.

In respect of the foregoing, the polygonal bounding wall configuration of chamber 128 enhances the aforementioned temperature uniformity and stability characteristics of the hybridization apparatus. Gas flows, e.g., those directed predominantly in the directions indicted by arrows A and C are directed along the respective wall surfaces of vertical side wall 150 (resulting from the flow stream of gas generally along the direction of arrow A) and floor 116 (resulting from the flow of gas from the discharge unit 133 in the direction indicated generally by arrow C. The directed gas flows of heated gas, e.g., air, then travel circumferentially about the inner bounding wall surfaces of the chamber 128, and the generally domed upper portion of the apparatus causes the gas to be broken up from its uniform flow direction and induces a highly effective internal circulation of heated gas which further minimizes the occurrence of temperature gradients within the interior volume of chamber 128, and provides enhanced temperature stability and uniformity within the aforementioned tolerance level (about ±0.5° C.).

For the purpose of inducing the highly efficient internal circulation of heated gas throughout the interior volume and the carousel disposed therein use, it is desirable to construct the housing so that the bounding walls of chamber 128 include at least one obtuse included angle between adjacent wall segments, as in the polygonal upper wall structure shown in FIGS. 1 and 2.

Thus, the invention contemplates a highly efficient hybridization apparatus wherein the chamber structure and geometry produce a highly efficient circulation of heated gas in the chamber of the apparatus, and in the practice of the invention, heated gas preferably is introduced in such a manner as to enhance such internal circulatory flows of gas, for maintenance of constant temperature conditions at a selected temperature value within the aforementioned low tolerance level.

It will be recognized that the geometry and configuration of the incubator chamber may be widely varied in the broad practice of the present invention, as an alternative to the specific polygonal structures shown in FIGS. 1 and 2, and that independently, heated gas may be introduced to the chamber in any suitable manner which is productive of enhanced flow and circulation of gas within the interior volume of the chamber.

For example, depending on the size and character of the incubator apparatus, it may be satisfactory in some instances to provide only a unidirectional introduction of gas into the incubator chamber. For example, referring to FIG. 2, it may be satisfactory in some instances to introduce a heated gas stream predominantly or even solely in the direction indicated by arrow A, and with the carousel 131 (see FIG. 1) being rotated in a clockwise direction, opposite to the direction of gas flow introduction along vertical side wall 150. By this opposing arrangement, the movement of the carousel opposes the flowed direction of the influent gas and creates an increased dispersion of the heated gas in the incubator chamber and enhanced temperature uniformity and stability, relative to a chamber lacking such "opposed direction" arrangement of the heated gas introduction means and the carousel.

Referring again to FIG. 1, the incubator chamber 128 is bounded at its front face by the door 122 which comprises a frame 124 and a transparent window 126, which may be of tempered glass, either single pane or preferably double pane, of a suitable heat resistance character. The door 122 may be hingedly joined to the associated housing wall 106, as for example by means of the hinge members 107 and 109 shown in FIG. 2, to provide a front-loading capability for the appartus. Correspondingly, the door 122 may be equipped with latch or securement means on its right-hand portion, such as a magnetic latch disposed on the inner side surface of the frame at the right-hand portion thereof, and matable with a corresponding magnetic strike plate or other suitable closure means cooperatively therewith.

The door 122 preferably is constructed and arranged to fit leak-tightly or at least to have a low gas leakage character with respect to the joint between the door and the housing when the door is closed and the hybridization apparatus is in operation.

As illustrated in FIGS. 1 and 2, and electronics/control module 104 is mounted in side-by-side relation to the main incubator module 102. The electronic/control module 104 may be constructed as a separate or separable unit, or alternatively it may be fixedly secured to the vertical wall 108 of housing 106 to form a conjoint or unitary structure therewith.

The electronics/control module 104 includes a housing comprising side wall 142, main front wall 144, upper front wall 146, and top wall 147 featuring an electronics monitoring and control display 148 at the upper portion thereof, as shown. The monitoring and control display 148 is suitably joined to electronics and circuitry means disposed within the housing of module 104, and connected by suitable signal transmission and control signal transmission to the appertaining elements in housing 106, which as mentioned may be disposed within housing 106 in the lower portion thereof behind front panel 138. On the main front wall 144 of the electronic/control module 104 is provided a grill 145 behind which is provided an exhaust fan, for cooling of the monitoring and control elements disposed within the electronics/control module housing.

Figure 3:
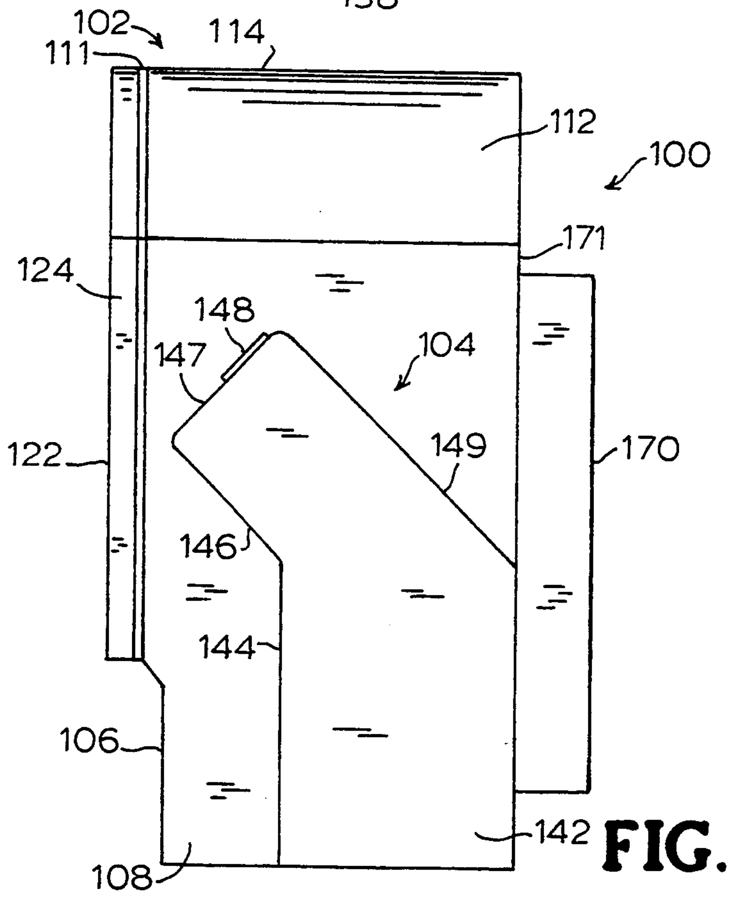
FIG. 3 is a side elevation view of the hybridization incubator of FIG. 1.

FIG. 3 is a side elevation view of the incubator apparatus of FIGS. 1–2, showing the configuration and details thereof. As shown, the electronics/control module 104 features a side wall 142 joined at its front edge to front main wall 144 and upper front wall 146. The module 104 includes an upper rear wall 149 and upper front wall 147 having the monitoring/control display 148 mounted thereon. The door 122 frontally encloses the incubator chamber (not shown in FIG. 3), with the door frame 124 providing a close fit with the housing 106, by means of insulation seal 111 on the inner circumferential surface of frame 124.

At the rear wall 171 of the housing 106 is joined a sub-housing 170 which accommodates the drive means employed to motively rotate the carousel, as hereinafter more fully described with reference to FIGS. 4 and 5 hereof.

Figure 4:
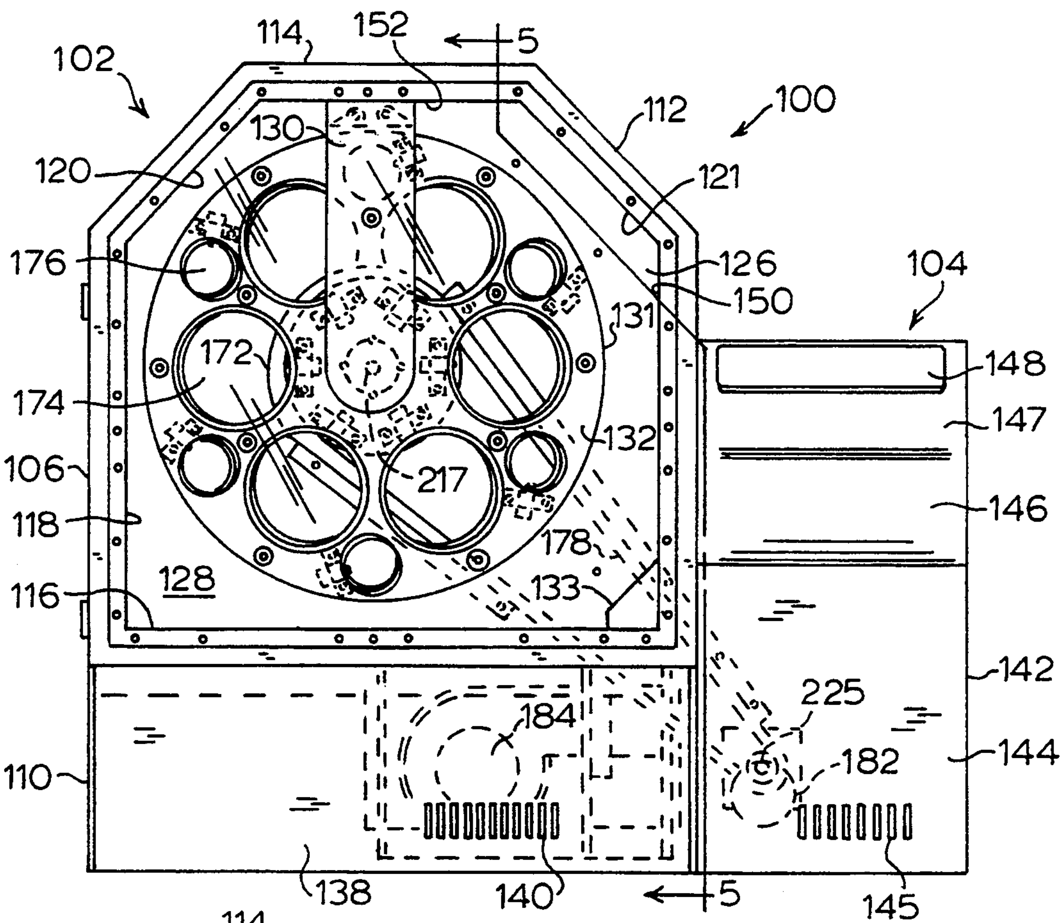
FIG. 4 is a front elevation view of the hybridization incubator of FIG. 1, showing the details of the carousel structure and the carousel drive means and heated air introduction means.
Figure 5:
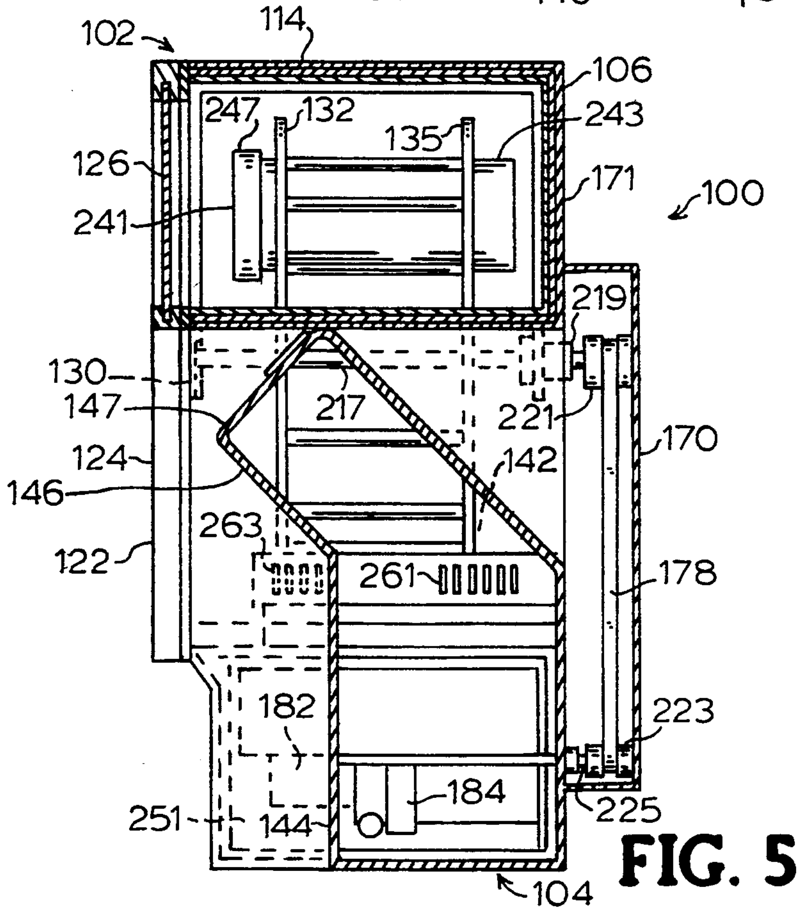
FIG. 5 is a side elevation view of the hybridization incubator shown in FIG. 4, showing the details of the carousel drive means.

Referring now to FIGS. 4 and 5, FIG. 4 is a front elevation view, and FIG. 5 a side elevation view, of the incubator apparatus of FIGS. 1–3, showing the details of the internal structure thereof, in a simplified, partially schematic fashion.

The corresponding parts and elements in FIGS. 4 and 5 are numbered correspondingly with respect to the same or corresponding features of FIGS. 1–3.

As shown in FIG. 4, the main incubator module 100 features carousel 131 mounted by means of cylindrical spindle assembly 172 at the lower portion of support 130, with the shaft 217 of the carousel spindle being generally horizontally aligned and extending through the bearing 219 at the rear wall 171 of housing 106, the shaft within the sub-housing 170 being joined to a driven pulley 221 fixedly mounted on shaft 217 and driven by drive belt 178 secured in turn to pulley 223 mounted on drive shaft 225, such drive shaft being connected to the drive motor 182 for driving of shaft 217 in a selected direction of rotation and at a selected rotational speed.

The carousel 131 as shown in FIG. 4 comprises a front, generally circular-shaped disk 132 having openings 174, of relatively larger diameter, and 176, of relatively smaller diameter, therein in a geometrically regular pattern about its periphery. The carousel also, as shown in FIG. 5 comprises a corresponding rear, generally circular disk 135 which is correspondingly constructed and is secured to the cylindrical spindle 172 in the same manner as disk member 132. The carousel provides a three-mode movement of the sample container during rotation of the carousel-rotation of the sample container about its own axis, rotation about the axis of the carousel spindle, and back-and-forth movement.

By this arrangement, the carousel 131 is constructed to accommodate the mounting of hybridization medium containers in the correspondingly sized openings 174, 176 of the carousel disks, so that containers, such as container 241 shown in FIG. 5 can be supportively maintained in the carousel and subjected to rotation during the rotary movement of the carousel to effect intimate mixing of the hybridization medium, as for example nucleic acid blots and buffer medium, or other reagents and hybridization components, as retained in such containers. The container 241 is shown as having a cylindrical body 243 and an enlarged cap 247 which is leak-tightly secured thereto.

As shown in FIGS. 4 and 5, a blower 184 is mounted in the plenum space 251 of housing 106, and this blower is joined in gas outflow relationship to the gas discharge unit 133 for introduction of heated gas into the interior volume 128 of the chamber bounded by interior wall surfaces of wall members 116, 118, 120, 150, 121, and 152. The discharge unit 133 may be suitably ported, vented, louvered, or otherwise constructed for appropriate gas discharge flow, and as previously discussed, this unit preferably is constructed to produce a multidirectional flow of the discharge gas, preferably including main directed flows along each of the associated (adjacent) wall surfaces (of wall members 116 and 150).

As illustrated in FIG. 4, the drive belt 178 is connected at one end to drive shaft 225 of drive motor 182, and is connected at its other end to the cylindrical spindle 172 and driven spindle shaft 217.

As also shown in FIG. 5, the housing may be further vented in any suitable manner, as for example is shown with reference to the side vents 261 and 263.

Figure 6:
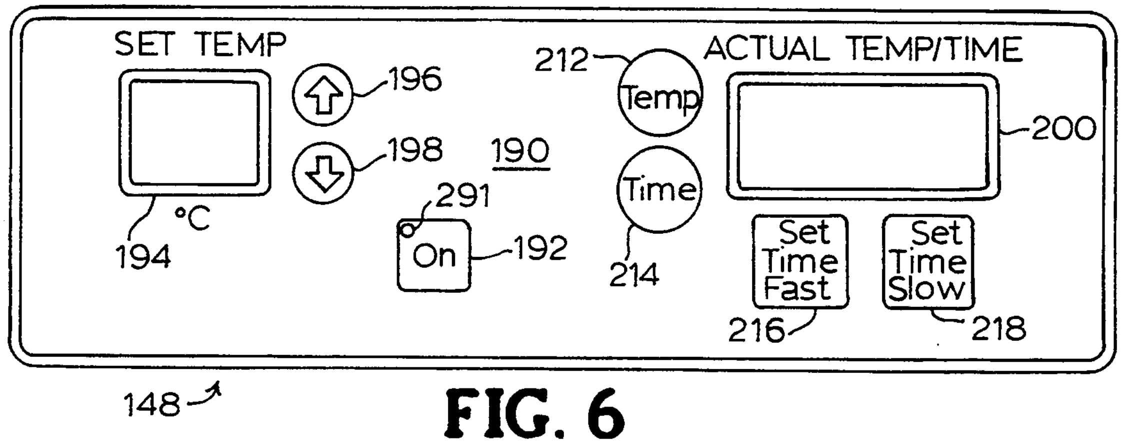
FIG. 6 is a front elevation view of a control panel employed with the electronic/control module of the hybridization incubator, of a type as shown in FIGS. 1–5.

FIG. 6 is a front elevation view of a monitoring/control display panel 148, of a type which may be used in connection with the electronics/control module 104 shown and described with reference to FIGS. 1–5 hereof.

As shown in FIG. 6, the monitoring/control display 148 on panel 190 features an on-off pressure switch 192, which may be a membrane switch or other suitable switch device which is manually actuatable. At the upper portion of the on-off switch 192 is a display light 291 which is illuminated when the electronic/control module is turned on. At the left-hand portion of the display is a digital temperature display 194 and to the right of such digital temperature display are temperature set point switches 196 and 198, switch 196 upon application of manual pressure thereto upwardly or increasingly incrementing the set point temperature by a predetermined increment, e.g., 1° C., and the switch 198 corresponding decreasing or decrementing the set point temperature value, as display on display 194.

On the right-hand portion of display 148 is provided a temperature/time readout display 200, and to the left of such readout display are time switch 214 and temperature 212, which may be selectively depressed to choose the display modality of display 200, as showing the time or the temperature, as desired.

Below temperature/time display 200 are sets switches 216 and 218. Switch 216 is a time set switch which is adapted for fast incrementing of the time, to select a rough time setting value, and switch 218 is a corresponding slow set switch for more closely selecting the desired time, so that switches 216 and 218 are in effect "rough" and "fine" time set switches.

In use, the display 148 may be actuated by the on-off switch 192, and the set point temperature for the incubation chamber may be set by means of set point switches 196 and 198 to display the desired set point temperature on display 194.

Subsequent to establishment of a desired set point temperature for the hybridization chamber, the time parameter of the hybridization operation and any appropriate time-temperature schedule (in the event the hybridization is carried out under more than one temperature value) is set by means of the time set switches 216 and 218, and the temperature is correspondingly reset for different phases of the multi-temperature hybridization sequence, by means of temperature set switches 196 and 198.

During the subsequent operation of the hybridization apparatus, the time switch 214 and temperature switch 212 may be alternatively actuated to display the actual temperature and elapsed time.

The display 148 shown in FIG. 6 may be associated with suitable microprocessor and microcircuitry elements of a type well known and within the skill of the art and the field of biomedical instrumentation. The temperature settings and time selections may thus be stored in the microprocessor and employed during the hybridization to selectively adjust the intensity of heating in the heating element associated with gas delivery means 184 (see FIG. 4), as for example a resistance heating element disposed in the inlet or outlet passage of the blower.

While the invention has been shown with respect to specific embodiments, features, and elements, it will be recognized that the invention may be widely varied and that other variations, modifications, and embodiments are possible within the broad scope of the invention, and accordingly all such variations modifications and embodiments are to be regarded as being within the spirit and scope of the invention.

What is claimed is:

1. A hybridization incubator comprising:

a housing including upper and side walls, a floor, a rear wall and a front door swingably openable to provide a front-loading character to the incubator, said housing walls, floor, and front door defining an enclosed incubator chamber of irregular polygonal geometric shape in elevational view, along a cross-section of the incubator chamber parallel to the rear wall, with the front door being parallel to the rear wall;

means for heating gas and circulating heated gas within said enclosed incubator chamber; and means for mounting hybridization medium containers and rotationally translating same in the enclosed incubator chamber, comprising a rotational carousel mounted in the enclosure incubator chamber on a central shaft member for rotation, said central shaft member (i) being mounted to extend between the rear wall and front door, (ii) being perpendicular to the rear wall and perpendicular to the front door, and (iii) being parallel to said floor, with said hybridization medium containers being front-loadable on and front-loadable from the carousel when the front door is open.

2. A hybridization incubator according to claim 1, wherein the incubator chamber includes at least two walls or wall segments defining an obtuse included angle between adjacent wall surfaces of the walls or wall segments.

3. A hybridization incubator according to claim 1, wherein the incubator chamber includes a polygonal, generally domed upper chamber portion defining an interior volume bounded by segmented wall surfaces forming at least one obtuse included angle between adjacent wall segments.

4. An incubator according to claim 1, wherein the gas heating and circulating means comprise a gas discharge structure producing bifurcated gas flow in the interior volume of the housing comprising opposingly directed gas flow streams over said segmented wall surfaces.

5. An incubator according to claim 1, wherein the front door is hingedly joined and fastenably secure to the walls.

6. An incubator according to claim 5, wherein the walls of the chamber are each planar, and include:

a horizontal floor wall;

two vertical side walls, each extending from a first end joined to a differing extremity of the floor wall, and extending upwardly to a second end, each of the side walls being of a same height;

two side angle walls, each joined at a first end thereof to the second end of a different vertical side wall, and extending angularly upwardly to a second end, with the second ends of the side angle walls being in transversely spaced-apart relationship to one another; and a horizontal top wall having first and second ends, with the first end of the horizontal top wall being joined to the second end of one of said side angle walls, and with the second end of the horizontal top wall being joined to the second end of the other of said side angle walls.

7. An incubator according to claim 6, wherein the included angle formed between each of the vertical side walls and the side angle wall joined thereto, is 120°, and the included angle formed between each of the side angle walls and the horizontal top wall is 120°.

8. An incubator according to claim 1, wherein the rotational carousel assembly is secured by a mounting structure to one of said segmented wall surfaces.

9. An incubator according to claim 1, wherein the rotational carousel comprises a cylindrical carousel, said central shaft member including a central cylindrical spindle with first and second ends, and a generally circular end plate coaxially joined to the central cylindrical spindle at each of the first and second ends, each generally circular end plate having a multiplicity of openings therein for receiving DNA sample containers, wherein the openings in each of the end plates are in axial registration with corresponding openings in the other end plate, wherein the openings are of circular shape, to accommodate the axial positioning of cylindrical sample containers therein such that end portions of a sample container repose in registered circular-shaped openings of the respective end plates.

10. An incubator according to claim 1, further comprising temperature controller means operatively coupled with the gas heating means for maintaining a selected gas temperature set point in the interior volume within the housing.

11. An incubator according to claim 10, wherein the temperature controller means comprises a microprocessor controller operatively coupled with said gas heating means, and said heating means comprising a resistance heater for heating of gas flowing through the resistance heater.

12. An incubator according to claim 1, further comprising means for generating an output of time/temperature conditions for gas in the interior volume within the housing.

13. An incubator according to claim 1, wherein the means for rotationally translating the rotational carousel are constructed and arranged to rotate the rotational carousel in a direction of rotation opposing the direction of gas flow of a gas flow stream in the interior volume within the housing.

14. An incubator according to claim 1, wherein the door of the housing is transparent, to visually verify and monitor performance of hybridization in the incubator.

* * * * *